United States Patent
Tung et al.

(10) Patent No.: US 9,777,009 B2
(45) Date of Patent: *Oct. 3, 2017

(54) DEUTERATED IBRUTINIB

(71) Applicant: CONCERT PHARMACEUTICALS, INC., Lexington, MA (US)

(72) Inventors: Roger D. Tung, Lexington, MA (US); Adam J. Morgan, Lexington, MA (US)

(73) Assignee: Concert Pharmaceuticals, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/220,642

(22) Filed: Jul. 27, 2016

(65) Prior Publication Data
US 2017/0015670 A1    Jan. 19, 2017

Related U.S. Application Data

(63) Continuation of application No. 14/418,831, filed as application No. PCT/US2013/052721 on Jul. 30, 2013, now Pat. No. 9,422,295.

(60) Provisional application No. 61/677,307, filed on Jul. 30, 2012.

(51) Int. Cl.
| | |
|---|---|
| *A01N 43/90* | (2006.01) |
| *A61K 31/519* | (2006.01) |
| *C07D 487/00* | (2006.01) |
| *C07D 487/04* | (2006.01) |
| *C07B 59/00* | (2006.01) |

(52) U.S. Cl.
CPC .......... *C07D 487/04* (2013.01); *C07B 59/002* (2013.01); *C07B 2200/05* (2013.01)

(58) Field of Classification Search
None
See application file for complete search history.

(56) References Cited

U.S. PATENT DOCUMENTS

| | | |
|---|---|---|
| 6,221,335 B1 | 4/2001 | Foster |
| 6,440,710 B1 | 8/2002 | Keinan et al. |
| 6,603,008 B1 | 8/2003 | Ando et al. |
| 7,514,444 B2 | 4/2009 | Honigberg et al. |
| 7,517,990 B2 | 4/2009 | Ito et al. |
| 7,732,454 B2 | 6/2010 | Verner |
| 9,212,285 B2 | 12/2015 | Biswal et al. |
| 9,422,295 B2 * | 8/2016 | Tung .................... C07D 487/04 |
| 2005/0069276 A1 | 3/2005 | Alken |
| 2007/0082929 A1 | 4/2007 | Gant et al. |
| 2007/0197695 A1 | 8/2007 | Potyen et al. |
| 2008/0103122 A1 | 5/2008 | Veltri |

FOREIGN PATENT DOCUMENTS

| | | |
|---|---|---|
| WO | WO 95/26325 A2 | 10/1995 |
| WO | WO 2004/111054 A1 | 12/2004 |
| WO | WO 2007/118651 A1 | 10/2007 |
| WO | WO 2008/039218 A2 | 4/2008 |
| WO | WO 2014/022390 A1 | 2/2014 |

OTHER PUBLICATIONS

Baille, T. A., "The Use of Stable Isotopes in Pharmacological Research," *Pharmacological Reviews*, 33(2): 81-132 (1981).
Browne, T. R., "Stable Isotope Techniques in Early Drug Development: An Economic Evaluation," *J. Clin. Pharmacol.*, 38: 213-220 (1998).
Cherrah, Y., et al., "Study of Deuterium Isotope Effects on Protein Binding by Gas Chromatography/Mass Spectrometry. Caffeine and Deuterated Isotopomers," *Biomedical and Environmental Mass Spectrometry*, 14: 653-657 (1987).
Dyck, L. E., et al., "Effects of Deuterium Substitution on the Catabolism of β-Phenylethylamine: An In Vivo Study," *Journal of Neurochemistry*, 46(2): 399-404 (1986).
Fisher, M.B. et al., "The Complexities Inherent in Attempts to Decrease Drug Clearance by Blocking Sites of CYP-Mediated Metabolism," Curr. Opin. Drug Discov. Devel., 9(1):101-109 (2006).
Foster, A. B., "Deuterium Isotope Effects in Studies of Drug Metabolism," *Trends in Pharmacological Sciences*, 5: 524-527 (1984).
Foster, A. B., "Deuterium Isotope Effects in the Metabolism of Drugs and Xenobiotics: Implications for Drug Design," *Advances in drug Research*, 14:1-40 (1985).

(Continued)

*Primary Examiner* — Jeffrey H Murray
(74) *Attorney, Agent, or Firm* — Hamilton, Brook, Smith & Reynolds, P.C.

(57) ABSTRACT

The present invention in one embodiment provides a compound of Formula I:

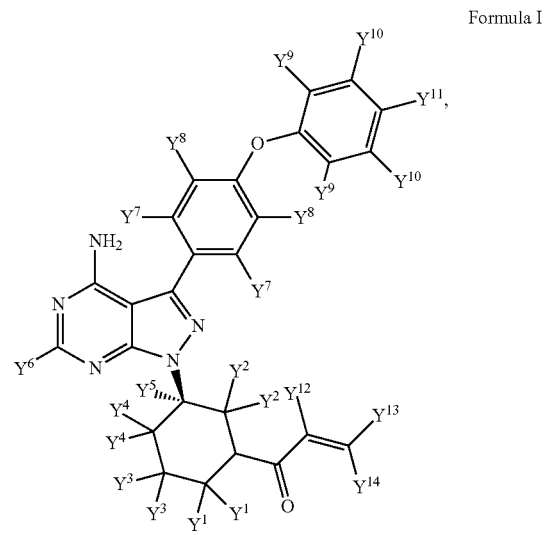

Formula I or a pharmaceutically acceptable salt thereof, wherein the variables shown in Formula I are as defined in the specification.

11 Claims, No Drawings

(56) References Cited

OTHER PUBLICATIONS

Gouyette, A., "Synthesis of Deuterium-labelled Elliptinium and its Use in Metabolic Studies," *Biomedical and Environmental Mass Spectrometry*, 15: 243-247 (1988).

Haskins, N. J., "The Application of Stable Isotopes in Biomedical Research," Biomedical Mass Spectrometry, 9(7): 269-277 (1982).

Honma S., et al., "The Metabolism of Roxatidine Acetate Hydrochloride," Drug Metabolism and Disposition, 15(4): 551-559 (1987).

Kushner, D.J. et al., "Pharmacological Uses and Perspectives of Heavy Water and Deuterated Compounds," *Can. J Physiol. Pharmacol.*, 77:79-88 (1999).

Notification Concerning Transmittal of International Preliminary Report on Patentability for International Application No. PCT/US2013/052721, dated Feb. 12, 2015, consisting of 6 pages.

Notification of Transmittal of the International Search Report and Written Opinion, for International Application No. PCT/US2013/052721, dated Oct. 1, 2013, consisting of 10 pages.

Pieniaszek, H. J., et al., "Moricizine Bioavailability via Simultaneous, Dual, Stable Isotope Administration: Bioequivalence Implications," J. Clin. Pharmacol, 39: 817-825 (1999).

Tonn G. R., et al., "Simultaneous Analysis of Diphenhydramine and a Stable Isotope Analog (2H10) Diphenhydramine Using Capillary Gas Chromatography with Mass Selective Detection in Biological Fluids from Chronically Instrumented Pregnant Ewes," Biological Mass Spectrometry, 22: 633-642 (1993).

Tung, Roger, The Development of Deuterium-Containing Drugs, Innovations in Pharmaceutical Technology, issue 32 (2010).

Wolen, R. L., "The Application of Stable Isotopes to Studies of Drug Bioavailability and Bioequivalence," J. Clin. Pharmacol., 26: 419-424 (1986).

* cited by examiner

DEUTERATED IBRUTINIB

RELATED APPLICATION

This application is a continuation of U.S. application Ser. No. 14/418,831, now U.S. Pat. No. 9,422,295 issued on Aug. 23, 2016, which is the U.S. National Stage of International Application No. PCT/US2013/052721, which designated the United States and was filed on Jul. 30, 2013, published in English, which claims the benefit of U.S. Provisional Application No. 61/677,307, filed on Jul. 30, 2012. The entire teachings of the above applications are incorporated herein by reference.

BACKGROUND OF THE INVENTION

Many current medicines suffer from poor absorption, distribution, metabolism and/or excretion (ADME) properties that prevent their wider use or limit their use in certain indications. Poor ADME properties are also a major reason for the failure of drug candidates in clinical trials. While formulation technologies and prodrug strategies can be employed in some cases to improve certain ADME properties, these approaches often fail to address the underlying ADME problems that exist for many drugs and drug candidates. One such problem is rapid metabolism that causes a number of drugs, which otherwise would be highly effective in treating a disease, to be cleared too rapidly from the body. A possible solution to rapid drug clearance is frequent or high dosing to attain a sufficiently high plasma level of drug. This, however, introduces a number of potential treatment problems such as poor patient compliance with the dosing regimen, side effects that become more acute with higher doses, and increased cost of treatment. A rapidly metabolized drug may also expose patients to undesirable toxic or reactive metabolites.

Another ADME limitation that affects many medicines is the formation of toxic or biologically reactive metabolites. As a result, some patients receiving the drug may experience toxicities, or the safe dosing of such drugs may be limited such that patients receive a suboptimal amount of the active agent. In certain cases, modifying dosing intervals or formulation approaches can help to reduce clinical adverse effects, but often the formation of such undesirable metabolites is intrinsic to the metabolism of the compound.

In some select cases, a metabolic inhibitor will be co-administered with a drug that is cleared too rapidly. Such is the case with the protease inhibitor class of drugs that are used to treat HIV infection. The FDA recommends that these drugs be co-dosed with ritonavir, an inhibitor of cytochrome P450 enzyme 3A4 (CYP3A4), the enzyme typically responsible for their metabolism (see Kempf, D. J. et al., Antimicrobial agents and chemotherapy, 1997, 41(3): 654-60). Ritonavir, however, causes adverse effects and adds to the pill burden for HIV patients who must already take a combination of different drugs. Similarly, the CYP2D6 inhibitor quinidine has been added to dextromethorphan for the purpose of reducing rapid CYP2D6 metabolism of dextromethorphan in a treatment of pseudobulbar affect. Quinidine, however, has unwanted side effects that greatly limit its use in potential combination therapy (see Wang, L et al., Clinical Pharmacology and Therapeutics, 1994, 56(6 Pt 1): 659-67; and FDA label for quinidine at www.accessdata.fda.gov).

In general, combining drugs with cytochrome P450 inhibitors is not a satisfactory strategy for decreasing drug clearance. The inhibition of a CYP enzyme's activity can affect the metabolism and clearance of other drugs metabolized by that same enzyme. CYP inhibition can cause other drugs to accumulate in the body to toxic levels.

A potentially attractive strategy for improving a drug's metabolic properties is deuterium modification. In this approach, one attempts to slow the CYP-mediated metabolism of a drug or to reduce the formation of undesirable metabolites by replacing one or more hydrogen atoms with deuterium atoms. Deuterium is a safe, stable, non-radioactive isotope of hydrogen. Compared to hydrogen, deuterium forms stronger bonds with carbon. In select cases, the increased bond strength imparted by deuterium can positively impact the ADME properties of a drug, creating the potential for improved drug efficacy, safety, and/or tolerability. At the same time, because the size and shape of deuterium are essentially identical to those of hydrogen, replacement of hydrogen by deuterium would not be expected to affect the biochemical potency and selectivity of the drug as compared to the original chemical entity that contains only hydrogen.

Over the past 35 years, the effects of deuterium substitution on the rate of metabolism have been reported for a very small percentage of approved drugs (see, e.g., Blake, M I et al, J Pharm Sci, 1975, 64:367-91; Foster, A B, Adv Drug Res 1985, 14:1-40 ("Foster"); Kushner, D J et al, Can J Physiol Pharmacol 1999, 79-88; Fisher, M B et al, Curr Opin Drug Discov Devel, 2006, 9:101-09 ("Fisher")). The results have been variable and unpredictable. For some compounds deuteration caused decreased metabolic clearance in vivo. For others, there was no change in metabolism. Still others demonstrated increased metabolic clearance. The variability in deuterium effects has also led experts to question or dismiss deuterium modification as a viable drug design strategy for inhibiting adverse metabolism (see Foster at p. 35 and Fisher at p. 101).

The effects of deuterium modification on a drug's metabolic properties are not predictable even when deuterium atoms are incorporated at known sites of metabolism. Only by actually preparing and testing a deuterated drug can one determine if and how the rate of metabolism will differ from that of its non-deuterated counterpart. See, for example, Fukuto et al. (J. Med. Chem. 1991, 34, 2871-76). Many drugs have multiple sites where metabolism is possible. The site(s) where deuterium substitution is required and the extent of deuteration necessary to see an effect on metabolism, if any, will be different for each drug.

SUMMARY OF THE INVENTION

This invention relates to novel derivatives of ibrutinib, an inhibitor of Bruton's tyrosine kinase (BTK) that is under active development for the treatment of chronic lymphocytic leukemia, mantle cell lymphoma and multiple myeloma. Ibrutinib may also be useful for treating non-Hodgkin's lymphoma, diffuse large B-cell lymphoma, and autoimmune disease. This invention also provides compositions comprising a compound of this invention and the use of such compositions in methods of treating diseases such as the foregoing.

Despite the potential beneficial activities of ibrutinib, there is a continuing need for new compounds to treat the aforementioned diseases and conditions.

DETAILED DESCRIPTION OF THE INVENTION

Definitions

The term "treat" means decrease, suppress, attenuate, diminish, arrest, or stabilize the development or progression of a disease (e.g., a disease or disorder delineated herein), lessen the severity of the disease or improve the symptoms associated with the disease.

"Disease" means any condition or disorder that damages or interferes with the normal function of a cell, tissue, or organ.

It will be recognized that some variation of natural isotopic abundance occurs in a synthesized compound depending upon the origin of chemical materials used in the synthesis. Thus, a preparation of ibrutinib will inherently contain small amounts of deuterated isotopologues. The concentration of naturally abundant stable hydrogen and carbon isotopes, notwithstanding this variation, is small and immaterial as compared to the degree of stable isotopic substitution of compounds of this invention. See, for instance, Wada, E et al., Seikagaku, 1994, 66:15; Gannes, L Z et al., Comp Biochem Physiol Mol Integr Physiol, 1998, 119:725.

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Also unless otherwise stated, when a position is designated specifically as "D" or "deuterium", the position is understood to have deuterium at an abundance that is at least 3000 times greater than the natural abundance of deuterium, which is 0.015% (i.e., at least 45% incorporation of deuterium).

The term "isotopic enrichment factor" as used herein means the ratio between the isotopic abundance and the natural abundance of a specified isotope.

In other embodiments, a compound of this invention has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

The term "isotopologue" refers to a species in which the chemical structure differs from a specific compound of this invention only in the isotopic composition thereof.

The term "compound," when referring to a compound of this invention, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound. However, as set forth above the relative amount of such isotopologues in toto will be less than 55% of the compound. In other embodiments, the relative amount of such isotopologues in toto will be less than 50%, less than 47.5%, less than 40%, less than 32.5%, less than 25%, less than 17.5%, less than 10%, less than 5%, less than 3%, less than 1%, or less than 0.5% of the compound.

The invention also provides salts of the compounds of the invention.

A salt of a compound of this invention is formed between an acid and a basic group of the compound, such as an amino functional group, or a base and an acidic group of the compound, such as a carboxyl functional group. According to another embodiment, the compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

The pharmaceutically acceptable salt may also be a salt of a compound of the present invention and a base. Exemplary bases include, but are not limited to, hydroxide of alkali metals including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methylamine, N-ethylamine; diethylamine; triethylamine; mono-, bis-, or tris-(2-OH—($C_1$-$C_6$)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like.

The compounds of the present invention (e.g., compounds of Formula I), may contain an asymmetric carbon atom, for example, as the result of deuterium substitution or otherwise. As such, compounds of this invention can exist as either individual enantiomers, or mixtures of the two enantiomers. Accordingly, a compound of the present invention may exist as either a racemic mixture or a scalemic mixture, or as individual respective stereoisomers that are substantially free from another possible stereoisomer. The term "substantially free of other stereoisomers" as used herein means less than 25% of other stereoisomers, preferably less than 10% of other stereoisomers, more preferably less than 5% of other stereoisomers and most preferably less than 2% of other stereoisomers are present. Methods of obtaining or synthesizing an individual enantiomer for a given compound are known in the art and may be applied as practicable to final compounds or to starting material or intermediates.

Unless otherwise indicated, when a disclosed compound is named or depicted by a structure without specifying the stereochemistry and has one or more chiral centers, it is understood to represent all possible stereoisomers of the compound.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" and "d" both refer to deuterium. "$d_{x-y}$" refers to substitution with from x to y number of deuterium atoms. "Stereoisomer" refers to both enantiomers and diastereomers. "Tert" and "t-" each refer to tertiary. "US" refers to the United States of America.

A group is "substituted with" a substituent when one or more hydrogen atoms of the group are replaced with a corresponding number of substituent atoms (if the substituent is an atom) or groups (if the substituent is a group). For example, "substituted with deuterium" refers to the replacement of one or more hydrogen atoms with a corresponding number of deuterium atoms.

Throughout this specification, a variable may be referred to generally (e.g., "each Y") or may be referred to specifically (e.g., $Y^1$, $Y^2$, $Y^3$, etc.). Unless otherwise indicated, when a variable is referred to generally, it is meant to include all specific embodiments of that particular variable.

Therapeutic Compounds

The present invention in one embodiment provides a compound of Formula I:

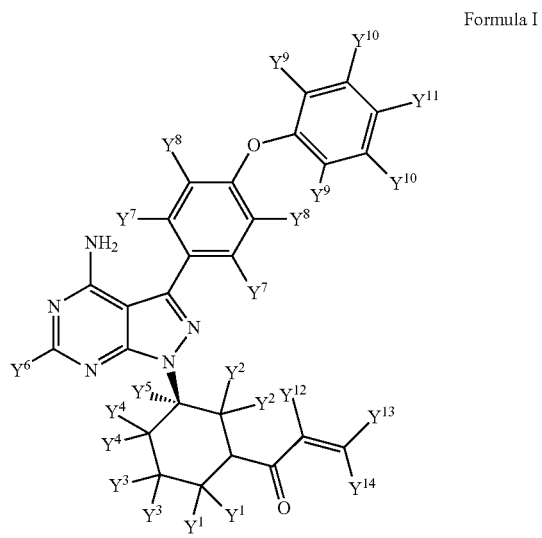

Formula I or a pharmaceutically acceptable salt thereof, wherein:
each Y is independently selected from hydrogen and deuterium,
provided that at least one Y is deuterium.

In one embodiment of the compound of Formula I, $Y^{12}$, $Y^{13}$, and $Y^{14}$ are each hydrogen. In one aspect of this embodiment, $Y^5$ is hydrogen. In another aspect, $Y^5$ is deuterium. In one aspect of this embodiment, each $Y^1$ is hydrogen. In another aspect of this embodiment, each $Y^1$ is deuterium. In one aspect of this embodiment, each $Y^2$ is hydrogen. In another aspect, each $Y^2$ is deuterium. In one aspect of this embodiment, each $Y^3$ is hydrogen. In another aspect, each $Y^3$ is deuterium. In one aspect of this embodiment, each $Y^4$ is hydrogen. In another aspect, each $Y^4$ is deuterium.

In one embodiment of the compound of Formula I, $Y^{12}$, $Y^{13}$, and $Y^{14}$ are each deuterium. In one aspect of this embodiment, $Y^5$ is hydrogen. In another aspect, $Y^5$ is deuterium. In one aspect of this embodiment, each $Y^1$ is hydrogen. In another aspect of this embodiment, each $Y^1$ is deuterium. In one aspect of this embodiment, each $Y^2$ is hydrogen. In another aspect, each $Y^2$ is deuterium. In one aspect of this embodiment, each $Y^3$ is hydrogen. In another aspect, each $Y^3$ is deuterium. In one aspect of this embodiment, each $Y^4$ is hydrogen. In another aspect, each $Y^4$ is deuterium.

In one embodiment of the compound of Formula I, $Y^5$ is hydrogen. In one aspect of this embodiment, each $Y^1$ is hydrogen. In another aspect of this embodiment, each $Y^1$ is deuterium. In one aspect of this embodiment, each $Y^2$ is hydrogen. In another aspect, each $Y^2$ is deuterium. In one aspect of this embodiment, each $Y^3$ is hydrogen. In another aspect, each $Y^3$ is deuterium. In one aspect of this embodiment, each $Y^4$ is hydrogen. In another aspect, each $Y^4$ is deuterium.

In one embodiment of the compound of Formula I, $Y^5$ is deuterium. In one aspect of this embodiment, each $Y^1$ is hydrogen. In another aspect of this embodiment, each $Y^1$ is deuterium. In one aspect of this embodiment, each $Y^2$ is hydrogen. In another aspect, each $Y^2$ is deuterium. In one aspect of this embodiment, each $Y^3$ is hydrogen. In another aspect, each $Y^3$ is deuterium. In one aspect of this embodiment, each $Y^4$ is hydrogen. In another aspect, each $Y^4$ is deuterium.

In one embodiment of the compound of Formula I, each $Y^1$ is hydrogen. In one aspect of this embodiment, each $Y^2$ is hydrogen. In another aspect, each $Y^2$ is deuterium. In one aspect of this embodiment, each $Y^3$ is hydrogen. In another aspect, each $Y^3$ is deuterium. In one aspect of this embodiment, each $Y^4$ is hydrogen. In another aspect, each $Y^4$ is deuterium.

In one embodiment of the compound of Formula I, each $Y^1$ is deuterium. In one aspect of this embodiment, each $Y^2$ is hydrogen. In another aspect, each $Y^2$ is deuterium. In one aspect of this embodiment, each $Y^3$ is hydrogen. In another aspect, each $Y^3$ is deuterium. In one aspect of this embodiment, each $Y^4$ is hydrogen. In another aspect, each $Y^4$ is deuterium.

In one embodiment of the compound of Formula I, each $Y^2$ is hydrogen. In one aspect of this embodiment, each $Y^3$ is hydrogen. In another aspect, each $Y^3$ is deuterium. In one aspect of this embodiment, each $Y^4$ is hydrogen. In another aspect, each $Y^4$ is deuterium.

In one embodiment of the compound of Formula I, each $Y^2$ is deuterium. In one aspect of this embodiment, each $Y^3$ is hydrogen. In another aspect, each $Y^3$ is deuterium. In one aspect of this embodiment, each $Y^4$ is hydrogen. In another aspect, each $Y^4$ is deuterium.

In one embodiment of the compound of Formula I, each $Y^3$ is hydrogen. In one aspect of this embodiment, each $Y^4$ is hydrogen. In another aspect, each $Y^4$ is deuterium.

In one embodiment of the compound of Formula I, each $Y^3$ is deuterium. In one aspect of this embodiment, each $Y^4$ is hydrogen. In another aspect, each $Y^4$ is deuterium.

In one embodiment of the compound of Formula I, each $Y^4$ is hydrogen. In another embodiment, each $Y^4$ is deuterium.

In one embodiment or in one aspect of any of the foregoing embodiments or aspects, each $Y^2$ is hydrogen and each $Y^4$ is hydrogen. In another embodiment or aspect, each $Y^2$ is deuterium and each $Y^4$ is deuterium.

In one embodiment or in one aspect of any of the foregoing embodiments or aspects, each $Y^7$ is hydrogen and each $Y^8$ is hydrogen. In another embodiment or aspect, each $Y^7$ is deuterium and each $Y^8$ is deuterium.

In yet another embodiment, the compound is a compound of Formula I selected from any one of the compounds (Cmpd) set forth in Table 1 (below):

TABLE 1

| Cmpd # | $Y^1$ | $Y^2$ | $Y^3$ | $Y^4$ | $Y^5$ | $Y^6$ | $Y^7 = Y^8$ | $Y^9 = Y^{10} = Y^{11}$ | $Y^{12} = Y^{13} = Y^{14}$ |
|---|---|---|---|---|---|---|---|---|---|
| 100 | D | H | H | H | H | H | H | H | H |
| 101 | H | H | H | H | D | H | H | H | H |
| 102 | D | H | H | H | D | H | H | H | H |
| 103 | H | D | H | D | H | H | H | H | H |
| 104 | D | D | H | D | H | H | H | H | H |
| 105 | H | D | H | D | D | H | H | H | H |
| 106 | D | D | H | D | D | H | H | H | H |
| 107 | D | D | D | D | D | H | H | H | H |
| 108 | D | D | H | D | H | D | H | H | H |
| 109 | D | D | D | D | D | D | H | H | H |
| 110 | H | H | H | H | H | D | H | H | H |
| 111 | D | H | H | H | H | H | H | H | D |
| 112 | H | H | H | H | D | H | H | H | D |
| 113 | D | H | H | H | D | H | H | H | D |
| 114 | H | D | H | D | H | H | H | H | D |
| 115 | D | D | H | D | H | H | H | H | D |
| 116 | H | D | H | D | D | H | H | H | D |
| 117 | D | D | H | D | D | H | H | H | D |
| 118 | D | D | D | D | D | H | H | H | D |
| 119 | D | D | H | D | H | D | H | H | D |
| 120 | D | D | D | D | D | D | H | H | D |
| 121 | H | H | H | H | H | D | H | H | D |
| 122 | H | H | H | H | H | H | H | H | D |
| 123 | H | H | H | H | H | D | D | H | H |
| 124 | H | H | H | H | H | H | D | H | H |
| 125 | H | H | H | H | H | H | H | D | H |
| 126 | H | H | H | H | H | H | D | D | D |
| 127 | D | D | D | D | D | H | D | D | H |
| 128 | D | D | D | D | D | H | D | D | D |
| 129 | D | D | D | D | D | D | D | D | H |
| 130 | D | D | D | D | D | D | D | D | D | or a pharmaceutically acceptable salt thereof, wherein any atom not designated as deuterium is present at its natural isotopic abundance.

In another set of embodiments, any atom not designated as deuterium in any of the embodiments, aspects, or examples set forth above is present at its natural isotopic abundance.

The synthesis of compounds of Formula I may be readily achieved by synthetic chemists of ordinary skill by reference to the Exemplary Synthesis and Examples disclosed herein. Relevant procedures analogous to those of use for the preparation of compounds of Formula I and intermediates thereof are disclosed, for instance in U.S. Pat. No. 7,732,454.

Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure.

Exemplary Synthesis

Scheme 1 provides an exemplary procedure for the preparation of the compounds of Formula I.

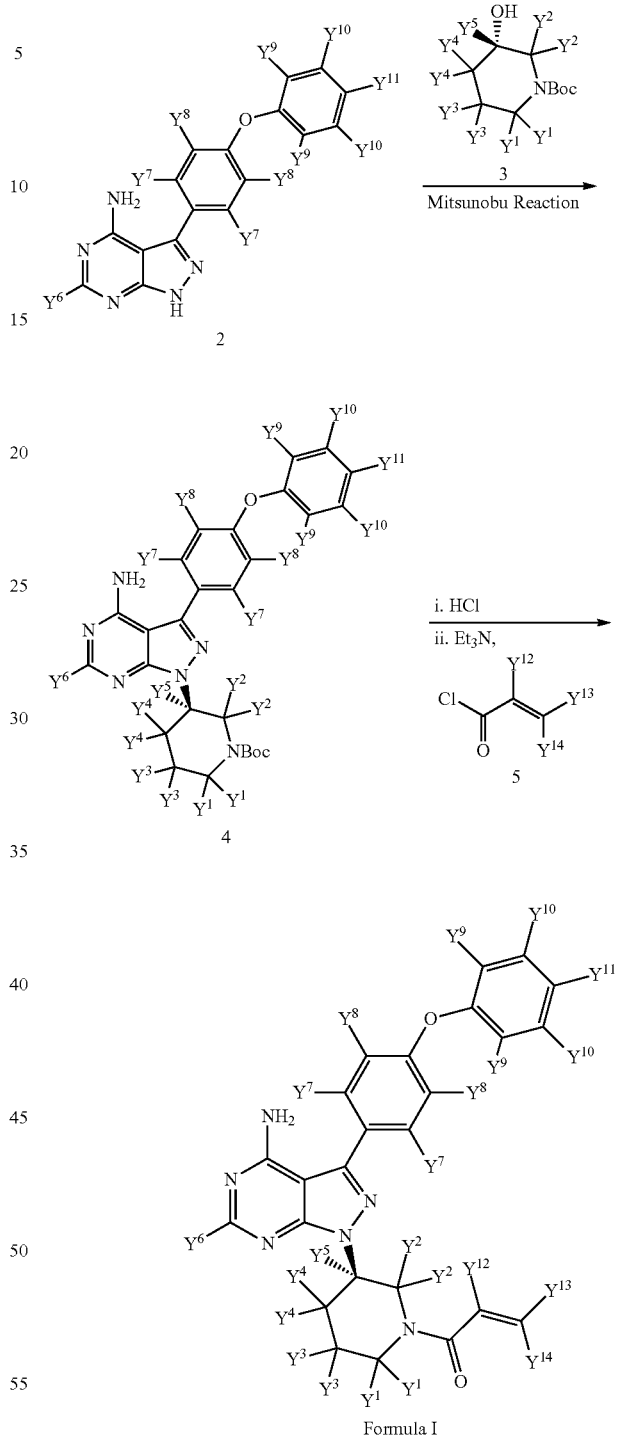

Scheme 1. Synthesis of Compounds of Formula I:

As shown in Scheme 1, appropriately deuterated 2 reacts with appropriately deuterated 3 under Mitsunobu reaction conditions in a manner analogous to Zhengying, P. et al., Chem. Med. Chem. 2007, 2, 58-61, to provide 4. Deprotection of 4 followed by acylation with appropriately deuterated 5 analogously to US patent publication 20080108636 gives a compound of Formula I.

Scheme 2 provides an exemplary procedure for the preparation of the compounds of formula 2 for use in Scheme 1.

Scheme 2. Synthesis of compound 2 (Scheme 1):

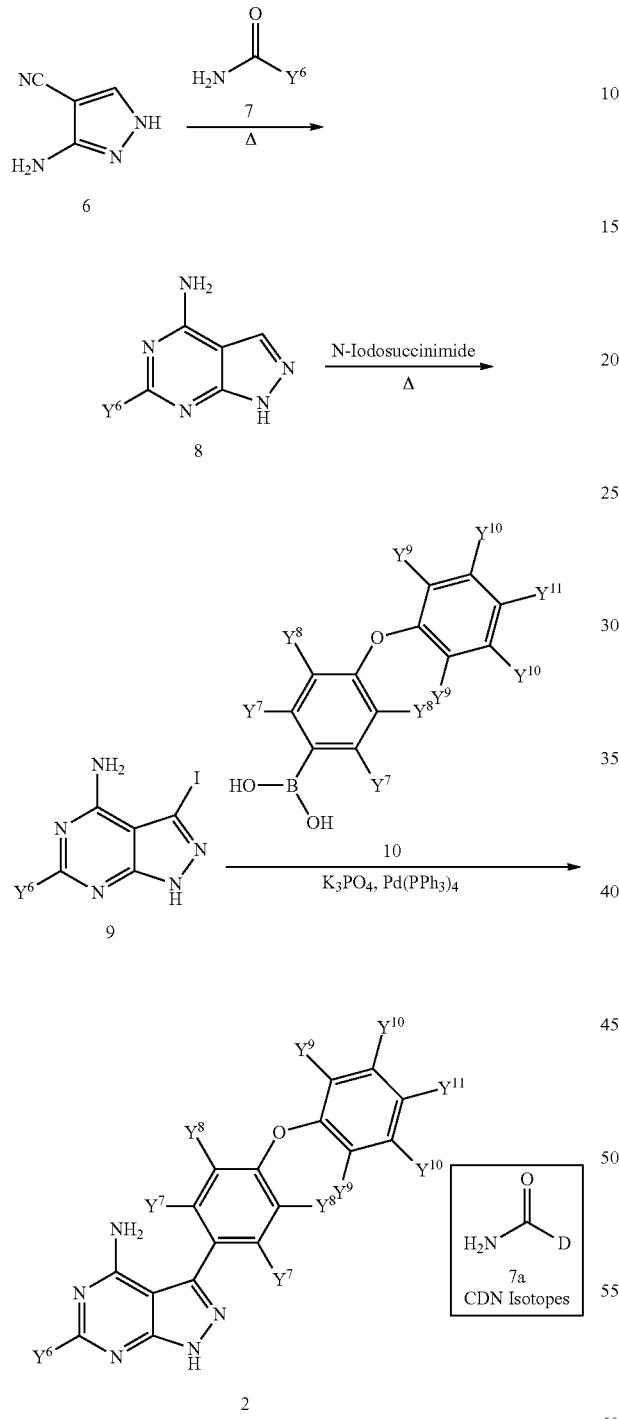

Scheme 3 provides an exemplary procedure for the preparation of the compounds of formula 10 for use in Scheme 2.

Scheme 3. Synthesis of compound 10 (Scheme 2):

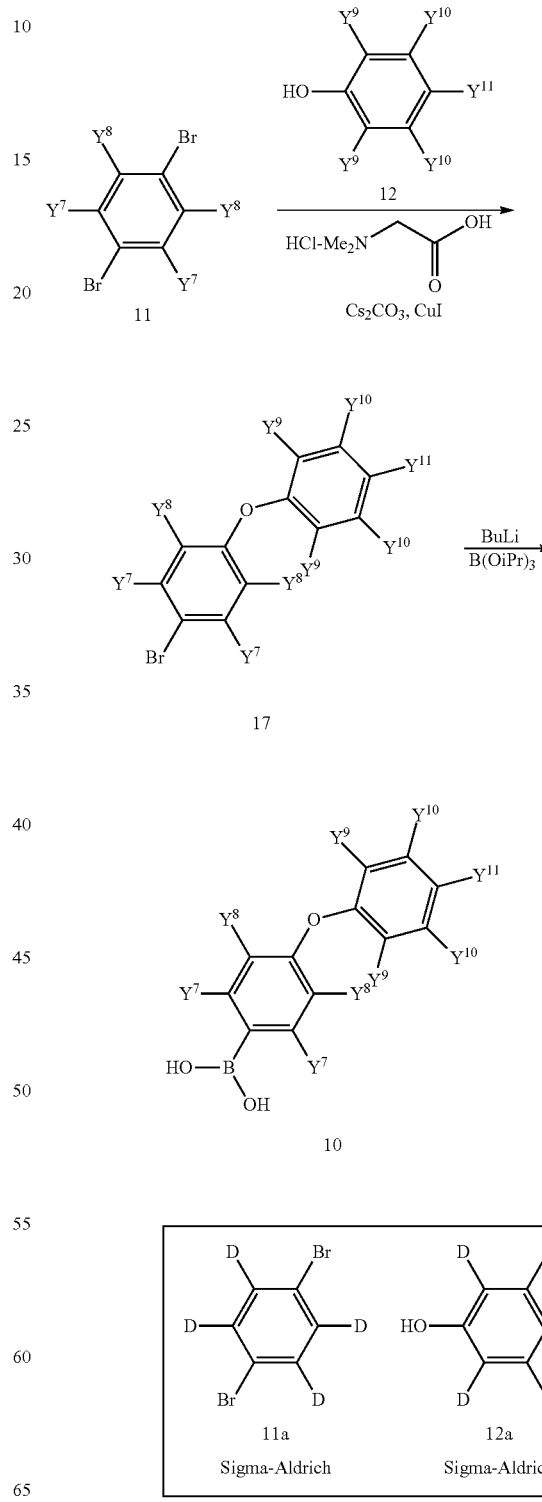

As shown in Scheme 2, 2 may be prepared starting with 6 using a procedure analogous to what is described in patent publication WO 2012003544. 6 is heated with appropriately deuterated 7 to afford 8, which is heated with N-iodosuccinimide to give 9. Reaction of 9 with 10 yields 2. A deuterated example of 7, compound 7a (shown in the inset of Scheme 2) is commercially available.

11a and/or 12a may be employed in Scheme 3 to afford compounds 10a, 10b and 10c.

Scheme 4a provides an exemplary procedure for the preparation of compound 3a for use in Scheme 1.

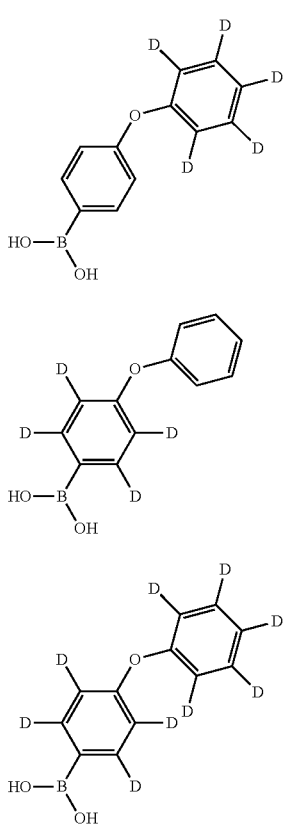

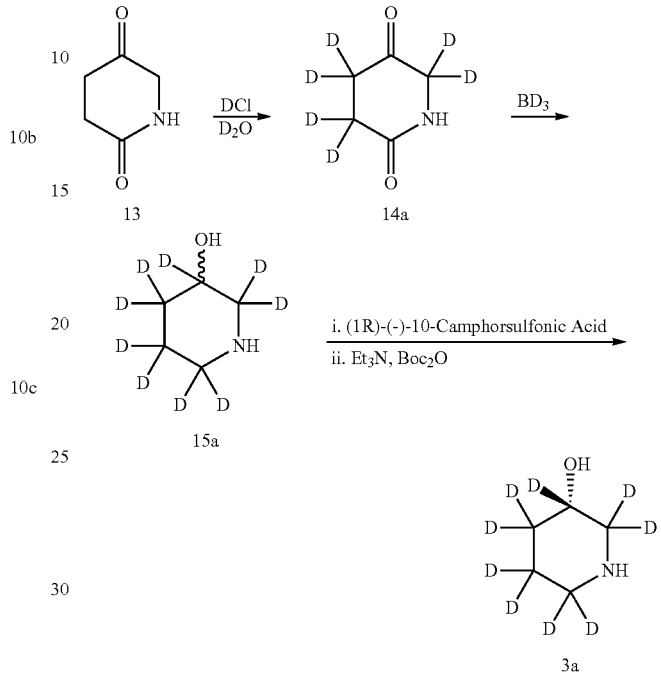

Scheme 4a. Preparation of 3a, an example of compound 3 (Scheme 1):

As shown in Scheme 3, appropriately deuterated 11 is treated with appropriately deuterated 12 using a procedure analogous to what is described in patent publication WO 2006125208 to give 17. 17 is treated with BuLi followed by B(OiPr)$_3$ to give 10. A deuterated example of 11, compound 11a (shown in the inset of Scheme 3) is commercially available. A deuterated example of 12, compound 12a (shown in the inset of Scheme 3) is commercially available.

As shown in Scheme 4, 13 is treated with DCl/D$_2$O to give 14a, which on treatment with BD$_3$ gives 15a. Chiral resolution of 15a followed by introduction of the Boc protecting group is accomplished in a manner analogous to that described in patent publication WO 2004072086 to give 3a.

Scheme 4b provides an exemplary procedure for the preparation of compounds 3b-3h for use in Scheme 1.

Scheme 4b. Preparation of 3b-3h, an examples of compound 3 wherein Y$^2$ = Y$^4$ (Scheme 1):

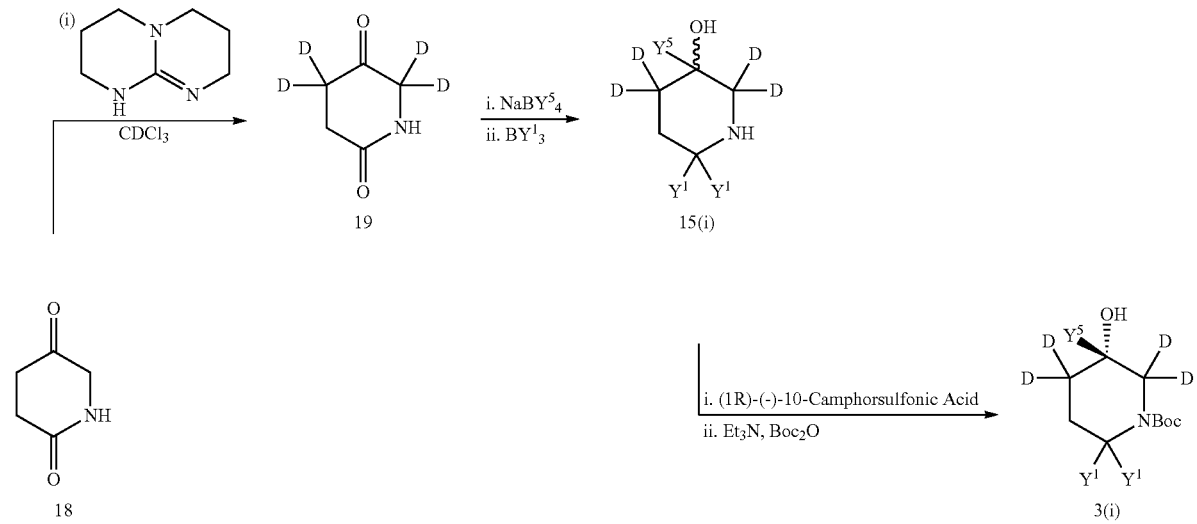

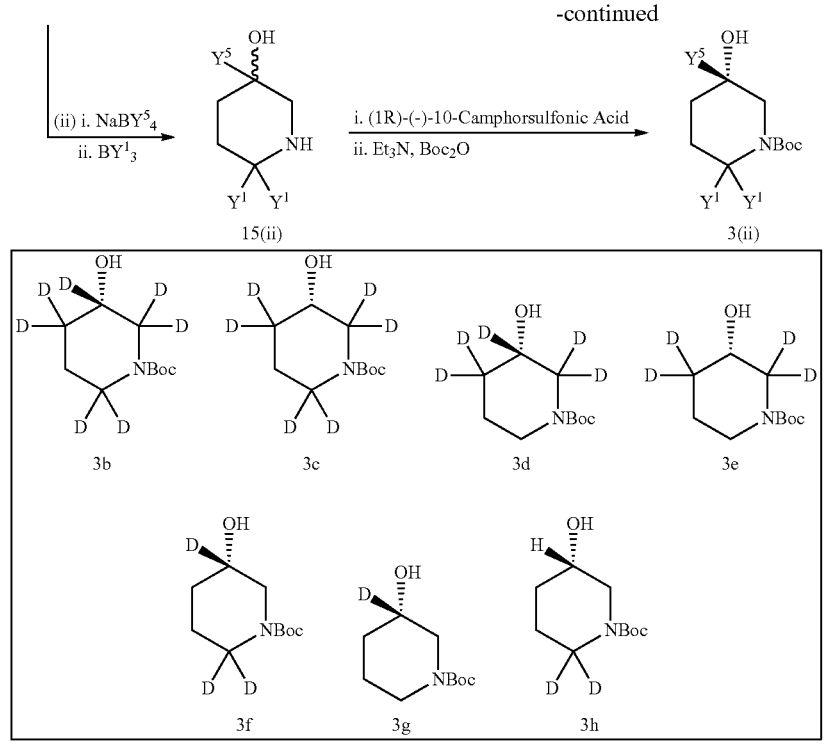

Compounds 3b-3h, where in each case the positions corresponding to $Y^4$ and $Y^2$ in Formula I are the same, may be prepared as shown in Scheme 4b. According to pathway (i), where each $Y^4$ and each $Y^2$ is deuterium, 18 is converted to 19 using a procedure analogous to what is described in Sabot, C. et al., *J. Org. Chem.* 2007, 72, 5001-5004. 19 is treated with $NaBY^5{}_4$ followed by $BY^1{}_3$ to give 15(i). Chiral resolution of 15(i) followed by introduction of the Boc protecting group is accomplished in a manner analogous to that described in patent publication WO 2004072086 to give 3(i). According to pathway (ii), where each $Y^4$ and each $Y^2$ is hydrogen, 18 is treated with $NaBY^5{}_4$ followed by $BY^1{}_3$ to give 15(ii). Chiral resolution of 15(ii) followed by introduction of the Boc protecting group is accomplished in a manner analogous to that described in patent publication WO 2004072086 to give 3(ii). Pathway (i) may be used to prepare compounds 3b-3e, while pathway (ii) may be used to prepare compounds 3f-3h (all shown in the inset of Scheme 4b).

Scheme 5 provides an exemplary procedure for the preparation of compound 5a for use in Scheme 1.

Scheme 5. Preparation of compound 5a, an example of compound 5 (Scheme 1):

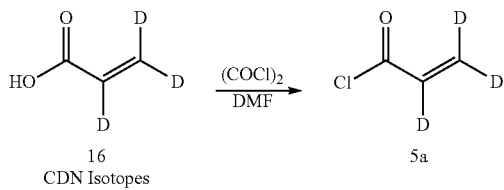

16
CDN Isotopes

5a

As shown in Scheme 5, commercially available 16 may be treated with oxalyl chloride to provide 5a in a manner analogous to that described in patent publication WO 2009005937 A1.

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (i.e., $R^1$, $R^2$, $R^3$, etc.) or not. The suitability of a chemical group in a compound structure for use in the synthesis of another compound is within the knowledge of one of ordinary skill in the art.

Additional methods of synthesizing compounds of Formula I and their synthetic precursors, including those within routes not explicitly shown in schemes herein, are within the means of chemists of ordinary skill in the art. Synthetic chemistry transformations and protecting group methodologies (protection and deprotection) useful in synthesizing the applicable compounds are known in the art and include, for example, those described in Larock R, *Comprehensive Organic Transformations*, VCH Publishers (1989); Greene, T W et al., *Protective Groups in Organic Synthesis*, 3$^{rd}$ Ed., John Wiley and Sons (1999); Fieser, L et al., *Fieser and Fieser's Reagents for Organic Synthesis*, John Wiley and Sons (1994); and Paquette, L, ed., *Encyclopedia of Reagents for Organic Synthesis*, John Wiley and Sons (1995) and subsequent editions thereof.

Combinations of substituents and variables envisioned by this invention are only those that result in the formation of stable compounds.

Compositions

The invention also provides pharmaceutical compositions comprising an effective amount of a compound of Formula I or pharmaceutically acceptable salt thereof, or a pharmaceutically acceptable salt of said compound; and a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this invention optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington: The Science and Practice of Pharmacy, Lippincott Williams & Wilkins, Baltimore, Md. (20th ed. 2000).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g.: Rabinowitz J D and Zaffaroni A C, U.S. Pat. No. 6,803,031, assigned to Alexza Molecular Delivery Corporation.

Topical administration of the pharmaceutical compositions of this invention is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

Thus, according to yet another embodiment, the compounds of this invention may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting said device with the coating composition described above. It will be obvious to those skilled in the art that the coating of the device will occur prior to implantation into a mammal.

According to another embodiment, the invention provides a method of impregnating an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

According to another embodiment, the invention provides an implantable drug release device impregnated with or containing a compound or a composition comprising a compound of this invention, such that said compound is released from said device and is therapeutically active.

Where an organ or tissue is accessible because of removal from the subject, such organ or tissue may be bathed in a medium containing a composition of this invention, a composition of this invention may be painted onto the organ, or a composition of this invention may be applied in any other convenient way.

In another embodiment, a composition of this invention further comprises a second therapeutic agent. The second therapeutic agent may be selected from any compound or therapeutic agent known to have or that demonstrates advantageous properties when administered with a compound having the same mechanism of action as ibrutinib. The second agent may be selected from of atumumab, rituximab, bendamustine, cyclophosphamide, doxorubicin, prednisone, vincristine sulfate, fludarabine, and allopurinol.

In another embodiment, the invention provides separate dosage forms of a compound of this invention and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to treat the target disorder.

The interrelationship of dosages for animals and humans (based on milligrams per meter squared of body surface) is described in Freireich et al., Cancer Chemother. Rep, 1966, 50: 219. Body surface area may be approximately determined from height and weight of the subject. See, e.g., Scientific Tables, Geigy Pharmaceuticals, Ardsley, N.Y., 1970, 537.

In one embodiment, an effective amount of a compound of this invention can range from 1 mg/kg to 50 mg/kg, administered once a day, such as 2.5 mg to 50 mg/kg, administered once a day, such as 2.5 mg to 25 mg/kg, administered once a day, such as 5 mg to 25 mg/kg, administered once a day.

In one embodiment, an effective amount of a compound of this invention can range from 1 mg/kg to 50 mg/kg, administered twice a day, such as 2.5 mg to 50 mg/kg, administered twice a day, such as 2.5 mg to 25 mg/kg, administered twice a day, such as 5 mg to 25 mg/kg, administered twice a day.

In one embodiment, an effective amount of a compound of this invention can range from 50 mg to 5000 mg, such as 100 mg to 2500 mg, such as 100 mg to 2250 mg, such as 150 mg to 2250 mg, such as 180 mg to 2250 mg. such as 300 mg to 100 mg, such as 350 mg to 800 mg, such as 400 mg to 600 mg, such as 450 mg, which can be administered once a day.

Effective doses will also vary, as recognized by those skilled in the art, depending on the diseases treated, the severity of the disease, the route of administration, the sex, age and general health condition of the subject, excipient usage, the possibility of co-usage with other therapeutic treatments such as use of other agents and the judgment of the treating physician.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

It is expected that some of the second therapeutic agents referenced above will act synergistically with the compounds of this invention. When this occurs, it will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

In another embodiment, the invention provides a method of inhibiting BTK in a cell, comprising contacting the cell with a compound of Formula I herein.

According to another embodiment, the invention provides a method of treating a disease selected from the group consisting of leukemia, including chronic lymphocytic leukemia; lymphoma, including mantle cell lymphoma; myeloma, including multiple myeloma; and autoimmune disease, comprising administering a pharmaceutical composition as described herein. In one embodiment, the disease is selected from the group consisting of chronic lymphocytic leukemia, mantle cell lymphoma, and multiple myeloma, non-Hodgkin's lymphoma, diffuse large B-cell lymphoma, and autoimmune disease.

Identifying a subject in need of such treatment can be in the judgment of a subject or a health care professional and can be subjective (e.g. opinion) or objective (e.g. measurable by a test or diagnostic method). In one embodiment the subject is a patient.

In another embodiment, any of the above methods of treatment comprises the further step of co-administering to the subject in need thereof one or more second therapeutic agents. The choice of second therapeutic agent may be made from any second therapeutic agent known to be useful for co-administration with ibrutinib. The choice of second therapeutic agent is also dependent upon the particular disease or condition to be treated. Examples of second therapeutic agents that may be employed in the methods of this invention are those set forth above for use in combination compositions comprising a compound of this invention and a second therapeutic agent. Such agents include but are not limited to of atumumab, rituximab, bendamustine, cyclophosphamide, doxorubicin, prednisone, vincristine sulfate, fludarabine, and allopurinol.

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention, comprising both a compound of the invention and a second therapeutic agent, to a subject does not preclude the separate administration of that same therapeutic agent, any other second therapeutic agent or any compound of this invention to said subject at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention, where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of a compound of Formula I alone or together with one or more of the above-described second therapeutic agents in the manufacture of a medicament, either as a single composition or as separate dosage forms, for treatment or prevention in a subject of a disease, disorder or symptom set forth above. Another aspect of the invention is a compound of Formula I for use in the treatment or prevention in a subject of a disease, disorder or symptom thereof delineated herein.

Example 1. Synthesis of (R)-1-(3-(4-Amino-3-(4-phenoxyphenyl)-1H-pyrazolo[3,4-d]pyrimidin-1-yl)piperidin-1-yl)prop-2-en-2,3,3-d$_3$-1-one (Compound 122)

Scheme 5. Preparation of Compound 122

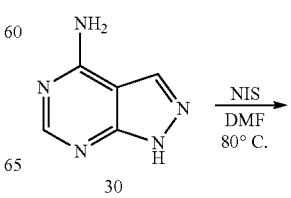

30

-continued

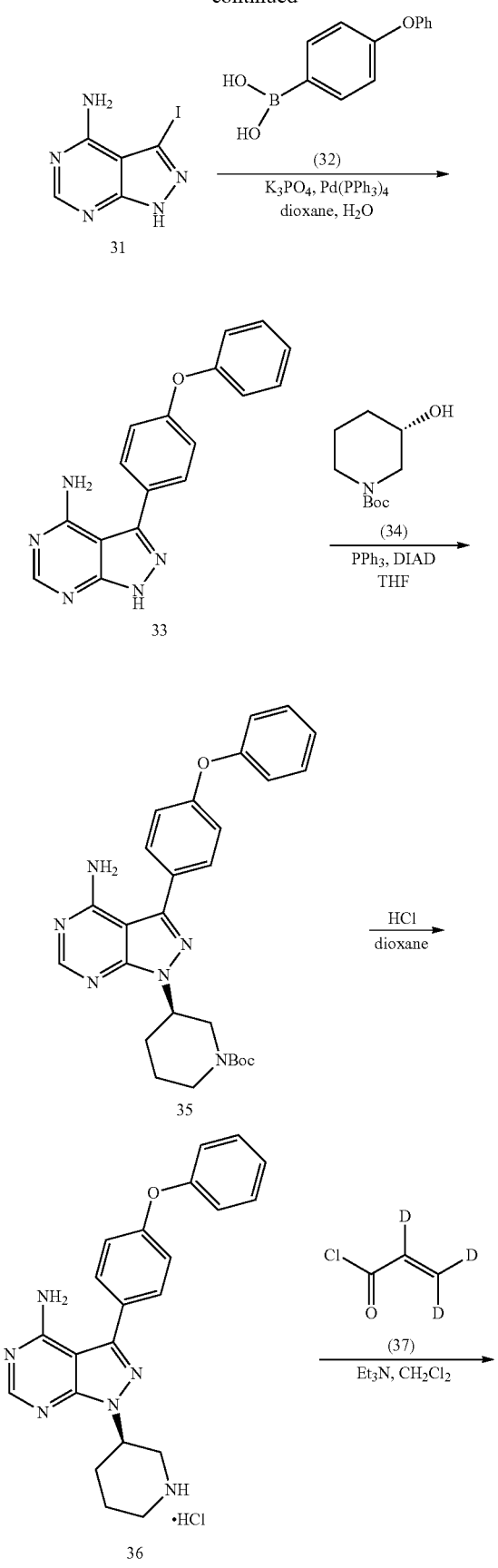

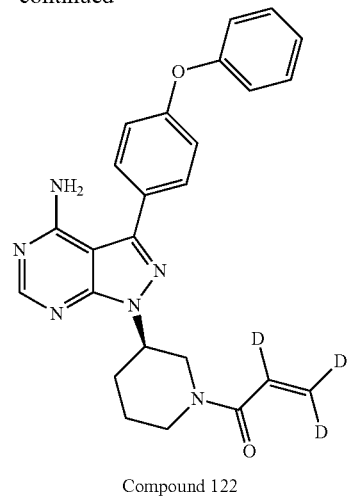

Compound 122

Step 1.
3-Iodo-1H-pyrazolo[3,4-d]pyrimidin-4-amine (31)

1H-Pyrazolo[3,4-d]pyrimidin-4-amine, 30 (5.0 g, 37 mmol, 1 equiv) was suspended in DMF (100 mL) and N-iodosuccinimide (NIS) (10.7 g, 45 mmol, 1.2 equiv) was added. The reaction was heated at 80° C. for 2 hours. The reaction was cooled to room temperature and then to 0° C. and was quenched by the drop-wise addition of water (200 mL). The resulting solids were collected by filtration, washed with water and cold ethanol, and dried in a vacuum oven to yield 31 (8.1 g, 84% yield) as a beige solid.

Step 2.
Phenoxyphenyl)-1H-pyrazolo[3,4-d]pyrimidin-4-amine (33)

Compound 31 (4.0 g, 15.3 mmol, 1 equiv), boronic acid 32 (6.56 g, 30.7 mmol, 2 equiv), and potassium phosphate tribasic monohydrate (10.56 g, 45.9 mmol, 3 equiv) were dissolved in dioxane (50 mL) and water (20 mL). The mixture was sparged with nitrogen for 20 minutes and tetrakis(triphenylphosphine)palladium (2.70 g, 2.3 mmol, 0.15 equiv) was added. The mixture was sparged with nitrogen for an additional 5 minutes and then heated at reflux for 24 hours. The reaction was cooled to room temperature and stirred overnight, giving a beige precipitate. The reaction mixture was diluted with water (50 mL) and the solids were collected by filtration. The crude product was triturated with methanol (150 mL) to yield 3.9 g of 85% pure product. The purity was further improved by trituration with ethyl acetate (100 mL), yielding 33 (3.6 g, 77% yield, 90% pure) as a beige solid.

Step 3. (R)-tert-Butyl 3-(4-amino-3-(4-phenoxyphenyl)-1H-pyrazolo[3,4-d]pyrimidin-1-yl)piperidine-1-carboxylate (35)

Compound 33 (1.80 g, 5.9 mmol, 1 equiv), protected piperidine, 34 (1.43 g, 7.1 mmol, 1.2 equiv), triphenylphosphine (2.33 g, 8.9 mmol, 1.5 equiv), and diisopropyl azodicarboxylate (1.80 g, 8.9 mmol, 1.5 equiv) were dissolved in THF (200 mL) and stirred at room temperature overnight. The reaction mixture was diluted with ethyl acetate (200 mL) and washed with saturated aqueous sodium bicarbonate (1×300 mL) and brine (1×300 mL). The organic layer was dried over sodium sulfate, filtered, and concentrated under reduced pressure. The crude material was adsorbed onto silica gel and purified using an Analogix automated chromatography system eluting with 0-8% methanol in dichloromethane. All fractions containing product were combined and re-chromatographed using the above conditions to yield 35 (1.1 g, 38% yield) as a white foam.

Step 4. (R)-3-(4-Phenoxyphenyl)-1-(piperidin-3-yl)-1H-pyrazolo[3,4-d]pyrimidin-4-amine hydrochloride (36)

Compound 35 (700 mg, 1.48 mmol, 1 equiv) was dissolved in dioxane (8 mL). A solution of hydrogen chloride in dioxane (4 mL of a 4 N solution in dioxane, 16 mmol, 10.7 equiv) was added and the reaction was stirred at room temperature overnight. The reaction was diluted with diethyl ether (20 mL) and the resulting solids were collected by filtration under a stream of nitrogen. The product was further dried in a vacuum oven to yield 36 (550 mg, 88% yield) as an off-white solid.

Step 5. (R)-1-(3-(4-Amino-3-(4-phenoxyphenyl)-1H-pyrazolo[3,4-d]pyrimidin-1-yl)piperidin-1-yl)prop-2-en-2,3,3-$d_3$-1-one (Compound 122)

A) DMF (0.003 mL, 0.03 mmol, 0.02 equiv) was added to commercially available acrylic acid-$d_4$ (126 mg, 1.66 mmol, 1 equiv, 99 atom % D) followed by oxalyl chloride (0.16 mL, 1.83 mmol, 1.1 equiv). The mixture was stirred for 30 minutes, at which point all gas evolution had ceased. The resulting acryloyl-$d_3$ chloride (37) was used as such.

B) In a 20 mL vial, triethylamine (0.46 mL, 3.18 mmol, 3 equiv) was added to a suspension of 36 (450 mg, 1.06 mmol, 1 equiv) in dichloromethane (10 mL). The reaction was stirred for 15 minutes, resulting in a clear solution. Acryloyl-$d_3$ chloride (37) (0.10 mL, 1.17 mmol, 1.1 equiv, prepared above) was then added and the reaction was stirred at room temperature for 2 hours. The reaction mixture was diluted with dichloromethane (50 mL) and washed with 5% citric acid (50 mL). The organic layer was dried over sodium sulfate, filtered, and concentrated under reduced pressure. The crude material was purified using an Analogix automated chromatography system eluting with 0-8% methanol in dichloromethane. All fractions containing product were pooled and concentrated to give a colorless film which was dissolved in benzene/methanol (5 mL) and lyophilized to yield Compound 122 (170 mg, 36% yield, [M+H]$^+$=444.3) as a white powder.

Example 2. Synthesis of (R)-1-(3-(4-Amino-3-(4-phenoxyphenyl)-1H-pyrazolo[3,4-d]pyrimidin-1-yl-6-$d_1$)piperidin-1-yl)prop-2-en-1-one (Compound 110)

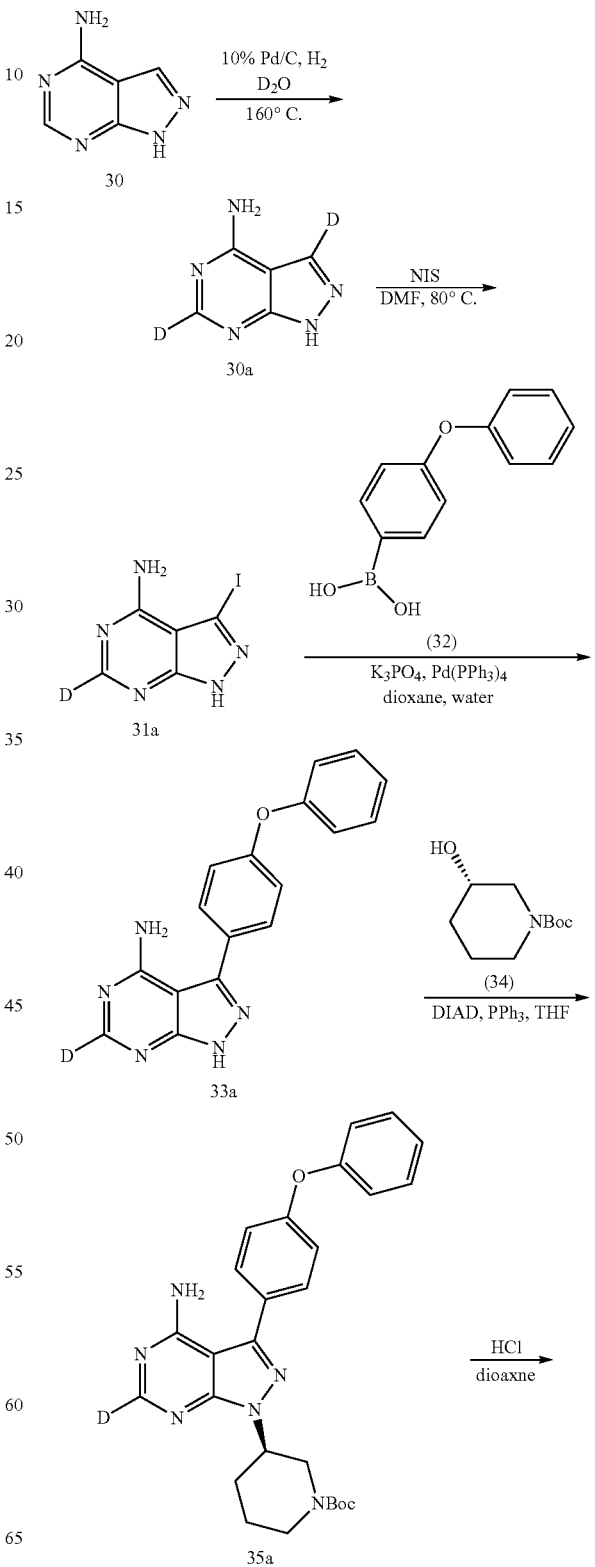

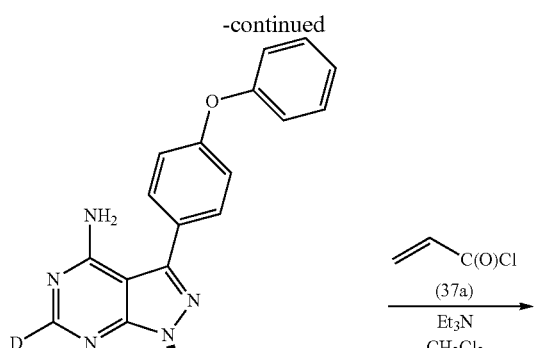

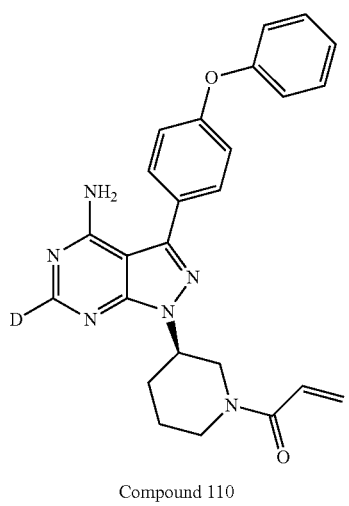

Compound 110

Step 1.
1H-pyrazolo[3,4-d]pyrimidin-4-amine-3,6-d$_2$ (30a)

A 2 L Parr bomb reactor was charged with 30 (5.0 g, 37 mmol, 1.0 equiv), 10% palladium on carbon (500 mg, dry), and D$_2$O (1 L, 99.8 atom % D). The reactor was evacuated and backfilled with hydrogen three times. After the final hydrogen charge to 20 psi the mixture was stirred at room temperature for 30 minutes. The hydrogen was then evacuated and replaced with nitrogen. The reactor was heated at 140° C. for 32 hours, at which point the reaction was complete as determined by MS analysis. The reaction was cooled to room temperature and transferred to a 3 L round bottom flask. Concentrated HCl (15 mL) was added and the mixture was heated to reflux. Once all of the solid product had dissolved, the mixture was filtered hot through a pad of celite, washing with water. While still hot, the pH of the filtrate was adjusted to 8 with concentrated ammonium hydroxide. The filtrate was cooled to room temperature and concentrated under reduced pressure to ~50% of the original volume. The resulting white solid was collected by filtration and dried in a vacuum oven to yield 30a (2.0 g, 40% yield) as a white solid. Additional product remained in the filtrate.

Step 2. 3-Iodo-1H-pyrazolo[3,4-d]pyrimidin-4-amine-6-d$_1$ (31a)

Compound 30a (1.0 g, 7.3 mmol, 1 equiv) was suspended in DMF (20 mL) and N-iodosuccinimide (NIS) (1.97 g, 8.7 mmol, 1.2 equiv) was added. The reaction was heated at 80° C. for 2 hours, an additional portion of NIS (1.0 g) was added and the reaction was heated at 80° C. for another 2 hours. The reaction was cooled to room temperature and then to 0° C. and was quenched by the drop-wise addition of water (60 mL). The resulting solids were collected by filtration and washed with water. The crude product was purified by trituration with cold ethanol (100 mL) and dried in a vacuum oven to yield 31a (1.74 g, 91% yield) as a beige solid.

Step 3. 3-(4-Phenoxyphenyl)-1H-pyrazolo[3,4-d]pyrimidin-4-amine-6-d$_1$ (33a)

Compound 31a (1.74 g, 6.6 mmol, 1 equiv), boronic acid 32 (2.85 g, 13.2 mmol, 2 equiv), and potassium phosphate tribasic (4.60 g, 19.9 mmol, 3 equiv) were dissolved in dioxane (20 mL) and water (8 mL). The mixture was sparged with nitrogen for 15 minutes and tetrakis(triphenylphosphine)palladium (1.15 g, 1.0 mmol, 0.15 equiv) was added. The mixture was sparged with nitrogen for an additional 5 minutes and then heated at reflux for 30 hours.

The reaction was cooled to room temperature and stirred overnight, giving a beige precipitate. The reaction mixture was diluted with water (60 mL) and the solids were collected by filtration. The crude product was triturated with methanol (50 mL), yielding 33a (900 mg, 45% yield) as a beige solid.

Step 4. (R)-tert-Butyl 3-(4-amino-3-(4-phenoxyphenyl)-1H-pyrazolo[3,4-d]pyrimidin-1-yl-6-d$_1$)piperidine-1-carboxylate (35a)

Compound 33a (840 mg, 2.75 mmol, 1 equiv), protected piperidine 34 (670 mg, 3.30 mmol, 1.2 equiv), triphenylphosphine (1.10 g, 4.13 mmol, 1.5 equiv), and diisopropyl azodicarboxylate (850 mg, 8.9 mmol, 1.5 equiv) were dissolved in THF (80 mL) and stirred at room temperature overnight. To force the reaction to completion, additional portions of 34 (670 mg), triphenylphosphine (1.10 g), and diisopropyl azodicarboxylate (850 mg) were added and the reaction was stirred an additional 6 hours. The reaction mixture was concentrated under reduced pressure. The crude material was adsorbed onto silica gel and purified using an Analogix automated chromatography system eluting with 0-8% methanol in dichloromethane. All fractions containing product were combined and re-chromatographed using the above conditions to yield 35a (160 mg, 12% yield) as a white solid. Additional less pure fractions were also recovered and retained.

Step 5. (R)-3-(4-Phenoxyphenyl)-1-(piperidin-3-yl)-1H-pyrazolo[3,4-d]pyrimidin-4-amine-6-d$_1$ hydrochloride (36a)

Compound 35a (160 mg, 0.33 mmol, 1 equiv) was dissolved in dioxane (10 mL). A solution of hydrogen chloride in dioxane (2 mL of a 4 N solution in dioxane, 8 mmol, 24 equiv) was added and the reaction was stirred at room temperature for 65 hours. The reaction was diluted with diethyl ether (40 mL) and the resulting solids were collected by filtration under a stream of nitrogen. The product was further dried in a vacuum oven to yield 36a (100 mg, 73% yield) as an off-white solid.

Step 6. (R)-1-(3-(4-Amino-3-(4-phenoxyphenyl)-1H-pyrazolo[3,4-d]pyrimidin-1-yl-6-d$_1$)piperidin-1-yl)prop-2-en-1-one (Compound 110)

A) DMF (0.014 mL, 0.18 mmol, 0.02 equiv) was added to acrylic acid (0.24 mL, 3.5 mmol, 1 equiv) followed by oxalyl chloride (0.33 mL, 3.8 mmol, 1.1 equiv). The mixture was stirred for 30 minutes, at which point all gas evolution had ceased. The resulting acryloyl chloride, 37a, was used as such.

B) Triethylamine (0.050 mL, 0.36 mmol, 3 equiv) was added to a suspension of 36a (50 mg, 0.12 mmol, 1 equiv) in dichloromethane (2.5 mL). The reaction was stirred for 15 minutes, resulting in a clear solution. Acryloyl chloride, 37a (0.011 mL, 0.13 mmol, 1.1 equiv, prepared above) was added and the reaction was stirred at room temperature for 2 hours to yield Compound 110 ([M+H]$^+$=442.)

Example 3. Synthesis of (R)-1-(3-(4-Amino-3-(4-phenoxyphenyl)-1H-pyrazolo[3,4-d]pyrimidin-1-yl-6-d$_3$-1-one (Compound 121)

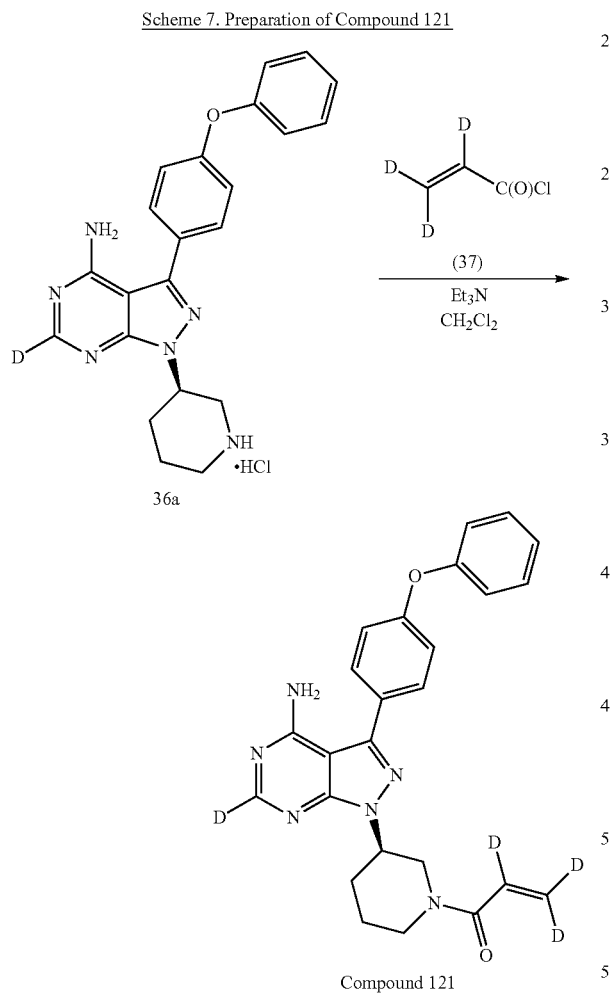

37 (0.011 mL, 0.13 mmol, 1.1 equiv, prepared above) was added and the reaction was stirred at room temperature for 2 hours to yield Compound 121 ([M+H]$^+$=445.)

Example 4. Synthesis of Intermediate (S)-tert-Butyl 3-hydroxy-2,2,3,4,4,5,5,6,6-d$_9$-piperidine-1-carboxylate (3a)

The synthesis of intermediate 3a is shown in Scheme 7 and described below.

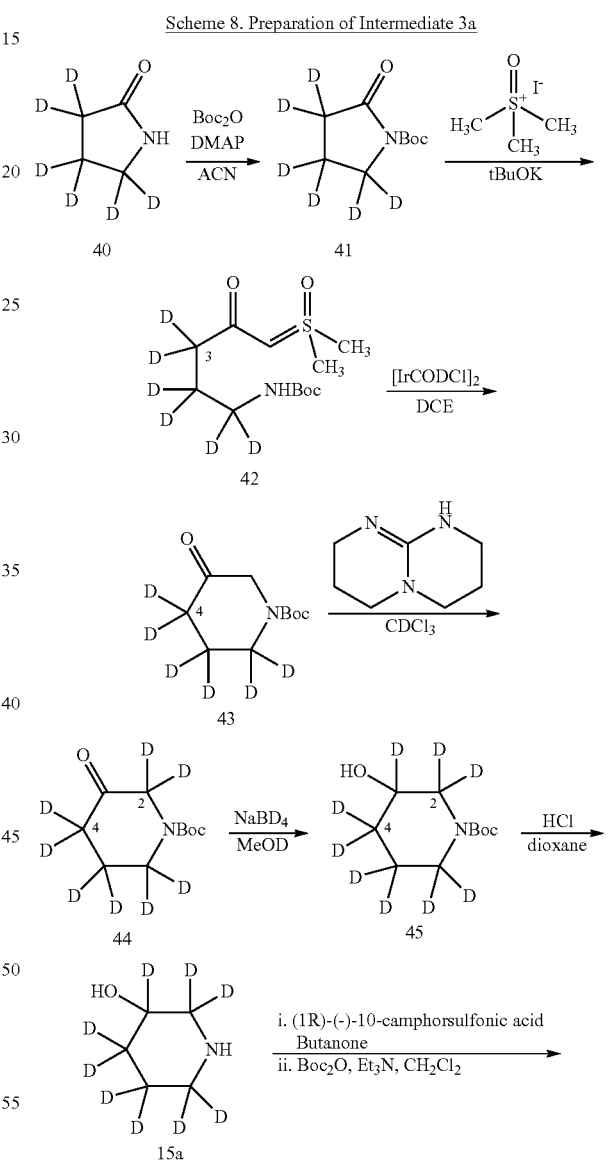

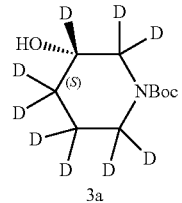

A) DMF (0.002 mL, 0.03 mmol, 0.02 equiv) was added to commercially available acrylic acid-d$_4$ (0.10 mL, 1.38 mmol, 1 equiv, 99 atom % D) followed by oxalyl chloride (0.12 mL, 1.52 mmol, 1.1 equiv). The mixture was stirred for 30 minutes, at which point all gas evolution had ceased. The resulting acryloyl-d$_3$ chloride, 37, was used as such.

B) Triethylamine (0.050 mL, 0.36 mmol, 3 equiv) was added to a suspension of 36a (50 mg, 0.12 mmol, 1 equiv) in dichloromethane (2.5 mL). The reaction was stirred for 15 minutes, resulting in a clear solution. Acryloyl-d$_3$ chloride,

Step 1. tert-Butyl 2-oxo-3,3,4,4,5,5-d$_6$-pyrrolidine-1-carboxylate (41)

Commercially available pyrrolidin-2-one, 40 (5.0 g, 55 mmol, 1 equiv, 98 atom % D) and 4-dimethylaminopyridine (740 mg, 6 mmol, 0.11 equiv) were dissolved in acetonitrile and cooled to 0° C. followed by the addition of di-tert-butyl dicarbonate (24.0 g, 110 mmol, 2 equiv). The reaction was allowed to warm to room temperature and stirred overnight. The reaction mixture was poured onto water (250 mL) and partially concentrated. The aqueous mixture was extracted with ethyl acetate (3×200 mL). The combined organic layers were washed with 1 N HCl (1×200 mL), saturated aqueous sodium bicarbonate (1×200 mL), and brine (1×200 mL). The organic layer was dried over sodium sulfate, filtered, and concentrated under reduced pressure. The crude product was purified using an Analogix automated chromatography system eluting with 20-80% ethyl acetate in heptanes to yield 41 (10.1 g, 96% yield) as a light yellow liquid.

Step 2. 4-Oxo-5-dimethylsulfoxonium-pentyl-1,1,2,2,3,3-d$_6$-carbamic acid tert-butyl ester (42)

Trimethyl sulfoxonium iodide (7.26 g, 33 mmol, 3 equiv) was suspended in THF (50 mL). Potassium tert-butoxide (5.09 g, 27.5 mmol, 2.5 equiv) was added and the reaction was heated at reflux for 2 hours. The white suspension was cooled to room temperature and 41 (2.1 g, 11.0 mmol, 1 equiv) was added. The reaction was stirred at room temperature for 2 hours and quenched by the addition of water (80 mL). The reaction mixture was extracted with 10% isopropanol in dichloromethane (4×100 mL). The combined organic layers were dried over sodium sulfate, filtered, and concentrated under reduced pressure. The crude product was dissolved in 2:1 ethyl acetate:heptanes (100 mL) and slowly concentrated to approximately 10 mL. The off white precipitate was collected by filtration, yielding 42 (2.2 g, 68% yield) as an off white solid. $^1$H NMR indicated approximately 50% proton incorporation at the 3 position.

Step 3. tert-Butyl 3-oxo-4,4,5,5,6,6-d$_6$-piperidine-1-carboxylate (43)

Bis(1,5-cyclooctadiene)diiridium(I) dichloride (47 mg, 0.071 mmol, 0.01 equiv) was dissolved in 1,2-dichloroethane and the solution was sparged with nitrogen for 15 minutes and then heated to reflux. In a separate flask, 42 (2.0 g, 7.1 mmol, 1 equiv) was dissolved in 1,2-dichloroethane and the solution was sparged with nitrogen for 15 minutes. This solution was then added drop-wise via syringe pump over 12 hours to the solution of catalyst at reflux. The reaction was heated at reflux for an additional hour upon completion of the addition. The reaction was cooled to room temperature and concentrated under reduced pressure. The crude material was purified using an Analogix automated chromatography system eluting with 0-40% ethyl acetate in heptanes to yield 43 (1.1 g, 76% yield) as a thick, colorless oil. $^1$H NMR indicated approximately 50% proton incorporation at the 4 position.

Step 4. tert-Butyl 3-oxo-2,2,4,4,5,5,6,6-d$_8$-piperidine-1-carboxylate (44)

Compound 43 (1.1 g, 5.9 mmol, 1 equiv) was dissolved in chloroform-d (100 mL, 99.8 atom % D) and 2,3,4,6,7,8-hexahydro-1H-pyrimido[1,2-a]pyrimidine (81 mg, 0.59 mmol, 0.1 equiv) was added. The reaction was stirred at room temperature for 16 hours, at which point $^1$H NMR indicated 10% H remaining at the 2 and 4 positions. The solvent was evaporated, fresh chloroform-d was added, and the reaction was stirred for an additional 16 hours. The cycle was then repeated a third time, at which point the reaction was diluted with dichloromethane (100 mL) and washed with 1 N HCl (1×100 mL). The organic layer was dried over sodium sulfate, filtered, and concentrated under reduced pressure to yield 44 (1.1 g, quantitative recovery) as a thick, colorless oil. No proton signal was detectable at either the 2 or 4 position by $^1$H NMR.

Step 5. tert-Butyl 3-hydroxy-2,2,3,4,4,5,5,6,6-d$_9$-piperidine-1-carboxylate (45)

Compound 44 (1.1 g, 5.3 mmol, 1 equiv) was dissolved in methanol-d (40 mL, 99 atom % D) and cooled to 0° C. Sodium borodeuteride (245 mg, 5.8 mmol, 1.1 equiv, 99 atom % D) was added. The reaction was stirred at 0° C. for 2 hours and then at room temperature overnight. The reaction was quenched with saturated ammonium chloride (5 mL) and water (10 mL). The mixture was partially concentrated and then extracted with dichloromethane (4×50 mL). The combined organic layers were dried over sodium sulfate, filtered, and concentrated under reduced pressure. The crude material was purified using an Analogix automated chromatography system eluting with 0-5% methanol in dichloromethane to yield 45 (0.50 g, 46% yield) as a thick, colorless oil which solidified upon standing.

Step 6. 3-Hydroxy-2,2,3,4,4,5,5,6,6-d$_9$-piperidine (15a)

Compound 45 (0.50 g, 2.4 mmol, 1 equiv) was dissolved in dioxane (5 mL) and hydrogen chloride was added (2 mL of a 4 N solution in dioxane, 8 mmol, 3.3 equiv). The reaction was stirred at room temperature overnight. The crude reaction was then concentrated under reduced pressure and 24% aqueous sodium hydroxide (5 mL) was added to the residue. The aqueous solution was extracted with 10% isopropanol in dichloromethane (6×50 mL). The combined organic layers were dried over sodium sulfate, filtered, and concentrated under reduced pressure to yield 15a (160 mg, 62% yield) as a colorless film.

Step 6. (S)-tert-Butyl 3-hydroxy-2,2,3,4,4,5,5,6,6-d$_9$-piperidine-1-carboxylate (Intermediate 3a)

A) Compound 15a (1 equiv) and (R)-camphorsulfonic acid (1 equiv) are heated to reflux in 2-butanone to obtain a clear solution. Upon cooling to room temperature a white solid precipitate is obtained which is filtered, washed with 2-butanone, and dried to yield the (R)-CSA salt of the S enantiomer of 15a. The optical purity is further improved by heating the isolated solid to reflux in a second portion of 2-butanone, cooling, filtering, and drying.

B) The (R)-CSA salt of the S enantiomer of 15a (1 equiv) and triethylamine (1.2 equiv) are dissolved in dichloromethane and cooled to 0° C. Di-tertbutyl dicarbonate (1.1 equiv) is added in one portion and the reaction is stirred at room temperature for 48 hours. The reaction mixture is diluted with dichloromethane and washed with water. The organic layer is dried, filtered, and concentrated. The crude material is purified by silica gel chromatography to yield 3a (S enantiomer). Intermediate 3a may be useful in the preparation of compounds of Formula I wherein each $Y^1$, each $Y^2$, each $Y^3$, each $Y^4$ and $Y^5$ is deuterium, such as Compounds 107, 109, 118 and 120, in a manner analogous to the one shown herein for compounds 110, 121 and 122, as a skilled artisan may readily envisage. For example, for the preparation of compound 107, the key intermediates would be compound 3a, 33 and 37a. For the preparation of compound 109, the key intermediates would be compound 3a, 33a and 37a. For the preparation of compound 118, the key intermediates would be compound 3a, 33 and 37. And for the preparation of compound 120, the key intermediates would be compound 3a, 33a and 37.

Example 5. Evaluation of Metabolic Stability

Microsomal Assay:

Human liver microsomes (20 mg/mL) are obtained from Xenotech, LLC (Lenexa, Kans.). β-nicotinamide adenine dinucleotide phosphate, reduced form (NADPH), magnesium chloride ($MgCl_2$), and dimethyl sulfoxide (DMSO) are purchased from Sigma-Aldrich.

Determination of Metabolic Stability:

7.5 mM stock solutions of test compounds are prepared in DMSO. The 7.5 mM stock solutions are diluted to 12.5-50 μM in acetonitrile (ACN). The 20 mg/mL human liver microsomes are diluted to 0.625 mg/mL in 0.1 M potassium phosphate buffer, pH 7.4, containing 3 mM $MgCl_2$. The diluted microsomes are added to wells of a 96-well deep-well polypropylene plate in triplicate. A 10 μL it aliquot of the 12.5-50 μM test compound is added to the microsomes and the mixture is pre-warmed for 10 minutes. Reactions are initiated by addition of pre-warmed NADPH solution. The final reaction volume is 0.5 mL and contains 0.5 mg/mL human liver microsomes, 0.25-1.0 μM test compound, and 2 mM NADPH in 0.1 M potassium phosphate buffer, pH 7.4, and 3 mM $MgCl_2$. The reaction mixtures are incubated at 37° C., and 50 μL it aliquots are removed at 0, 5, 10, 20, and 30 minutes and added to shallow-well 96-well plates which contain 50 μL of ice-cold ACN with internal standard to stop the reactions. The plates are stored at 4° C. for 20 minutes after which 100 μL it of water is added to the wells of the plate before centrifugation to pellet precipitated proteins. Supernatants are transferred to another 96-well plate and analyzed for amounts of parent remaining by LC-MS/MS using an Applied Bio-systems API 4000 mass spectrometer. The same procedure is followed for the non-deuterated counterpart of the compound of Formula I and the positive control, 7-ethoxycoumarin (1 μM). Testing is done in triplicate.

Data Analysis:

The in vitro $t_{1/2}$s for test compounds are calculated from the slopes of the linear regression of % parent remaining (ln) vs incubation time relationship.

in vitro $t_{1/2}=0.693/k$ k=−[slope of linear regression of % parent remaining (ln) vs incubation time]

Data analysis is performed using Microsoft Excel Software.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention.

What is claimed is:

1. A compound of Formula I:

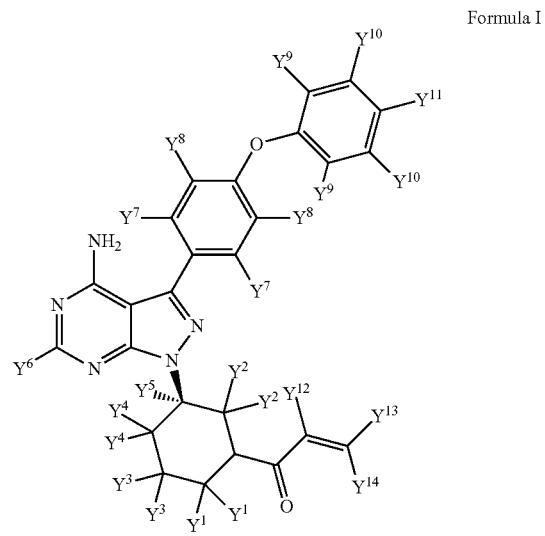

Formula I or a pharmaceutically acceptable salt thereof, wherein:
each $Y^1$, each $Y^2$, each $Y^3$, each $Y^4$, and $Y^5$ is deuterium; and
$Y^6$, each $Y^7$, each $Y^8$, each $Y^9$, each $Y^{10}$, $Y^{11}$, $Y^{12}$, $Y^{13}$, and $Y^{14}$ is independently selected from hydrogen and deuterium, wherein any atom not designated as deuterium is present at its natural isotopic abundance; and wherein the deuterium incorporation at each designated deuterium atom is at least 90%.

2. The compound of claim 1, wherein $Y^{12}$, $Y^{13}$, and $Y^{14}$ are each hydrogen.

3. The compound of claim 1, wherein $Y^{12}$, $Y^{13}$, and $Y^{14}$ are each deuterium.

4. The compound of claim 1, wherein each $Y^7$ is hydrogen and each $Y^8$ is hydrogen.

5. The compound of claim 1, wherein each $Y^7$ is deuterium and each $Y^8$ is deuterium.

6. The compound of claim 1, wherein the deuterium incorporation at each designated deuterium atom is at least 95%.

7. The compound of claim 1, wherein the deuterium incorporation at each designated deuterium atom is at least 97%.

8. The compound of claim 1, wherein the compound is selected from any one of the compounds (Cmpd) set forth in the table below:

| Cmpd # | $Y^1$ | $Y^2$ | $Y^3$ | $Y^4$ | $Y^5$ | $Y^6$ | $Y^7 = Y^8$ | $Y^9 = Y^{10} = Y^{11}$ | $Y^{12} = Y^{13} = Y^{14}$ |
|---|---|---|---|---|---|---|---|---|---|
| 107 | D | D | D | D | D | H | H | H | H |
| 109 | D | D | D | D | D | D | H | H | H |
| 118 | D | D | D | D | D | H | H | H | D |
| 120 | D | D | D | D | D | D | H | H | D |
| 127 | D | D | D | D | D | H | H | D | H |
| 128 | D | D | D | D | D | H | H | D | D |
| 129 | D | D | D | D | D | D | H | D | H |
| 130 | D | D | D | D | D | D | H | D | D | or a pharmaceutically acceptable salt thereof.

9. A pharmaceutical composition comprising the compound of claim 1 or a pharmaceutically acceptable salt thereof; and a pharmaceutically acceptable carrier.

10. A method of inhibiting BTK in a cell, comprising contacting the cell with a compound of claim 1.

11. A method of treating a disease selected from the group consisting of chronic lymphocytic leukemia, mantle cell lymphoma, and multiple myeloma, comprising administering to a subject in need of such treatment a compound of claim 1.

* * * * *